United States Patent
Horii et al.

(10) Patent No.: US 8,637,326 B2
(45) Date of Patent: Jan. 28, 2014

(54) BIOLOGICAL SUBSTANCE ANALYZING METHOD, AND BIOLOGICAL SUBSTANCE ANALYZING CELL, BIOLOGICAL SUBSTANCE ANALYZING CHIP, AND BIOLOGICAL SUBSTANCE ANALYZING APPARATUS EMPLOYED IN THE BIOLOGICAL SUBSTANCE ANALYZING METHOD

(75) Inventors: Kazuyoshi Horii, Kanagawa-ken (JP); Ryuichi Nakayama, Kanagawa-ken (JP); Yasutoshi Hirabayashi, Kanagawa-ken (JP)

(73) Assignee: Fujifilm Corporation, Tokyo (JP)

( * ) Notice: Subject to any disclaimer, the term of this patent is extended or adjusted under 35 U.S.C. 154(b) by 611 days.

(21) Appl. No.: 12/978,148

(22) Filed: Dec. 23, 2010

(65) Prior Publication Data
US 2011/0207238 A1  Aug. 25, 2011

(30) Foreign Application Priority Data
Feb. 25, 2010  (JP) ................................ 2010-040088

(51) Int. Cl.
*G01N 33/543* (2006.01)
(52) U.S. Cl.
USPC ............ 436/518; 422/401; 422/68.1; 422/73; 422/82.05; 422/502; 366/114; 435/287.2; 435/288.7; 436/524; 436/525
(58) Field of Classification Search
None
See application file for complete search history.

(56) References Cited

U.S. PATENT DOCUMENTS

| | | | |
|---|---|---|---|
| 4,575,485 A | 3/1986 | Sizto et al. | |
| 4,877,516 A | 10/1989 | Schram | |
| 7,980,752 B2 * | 7/2011 | Sarvazyan | 366/114 |
| 7,989,177 B2 * | 8/2011 | Bystryak et al. | 435/7.92 |
| 2002/0176804 A1 * | 11/2002 | Strand et al. | 422/100 |
| 2004/0069717 A1 * | 4/2004 | Laurell et al. | 210/748 |
| 2009/0052272 A1 * | 2/2009 | Sarvazyan | 366/116 |
| 2009/0053688 A1 * | 2/2009 | Bystryak et al. | 435/5 |

FOREIGN PATENT DOCUMENTS

| | | |
|---|---|---|
| EP | 0 767 376 A2 | 4/1997 |
| JP | 63-503370 A | 12/1988 |
| JP | 10-267927 A | 10/1998 |
| WO | WO 87/07178 A1 | 12/1987 |
| WO | WO 01/67084 A1 | 9/2001 |

OTHER PUBLICATIONS

Japanese Office Action dated Mar. 19, 2013, with partial English translation.

* cited by examiner

*Primary Examiner* — Chris L Chin
(74) *Attorney, Agent, or Firm* — McGinn IP Law Group, PLLC

(57) ABSTRACT

Detection of detection target substances at a sensor portion is expedited and the efficiency thereof is improved in biological substance analysis, to enable accelerated analysis with high sensitivity. A biological substance analyzing cell equipped with a reaction chamber having a sample supply space, an acoustic matching layer which is provided at a predetermined region of an inner wall of the reaction chamber that faces another inner wall, and a sensor portion provided within the reaction chamber is employed. Ultrasonic waves are emitted such that a standing wave are generated between the acoustic matching layer and the inner wall of the reaction chamber that faces the acoustic matching layer. The detection target substance is concentrated by the capturing forces of the standing waves, and the concentrated detection target substance is detected at the sensor portion.

10 Claims, 8 Drawing Sheets

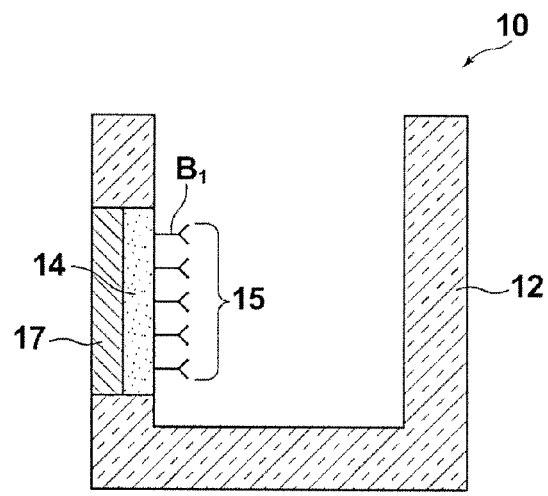
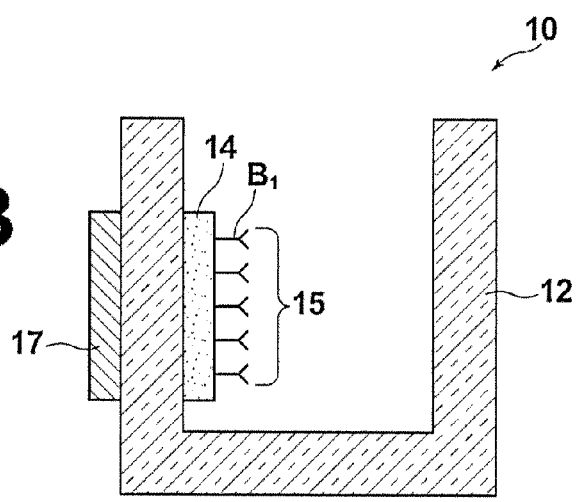
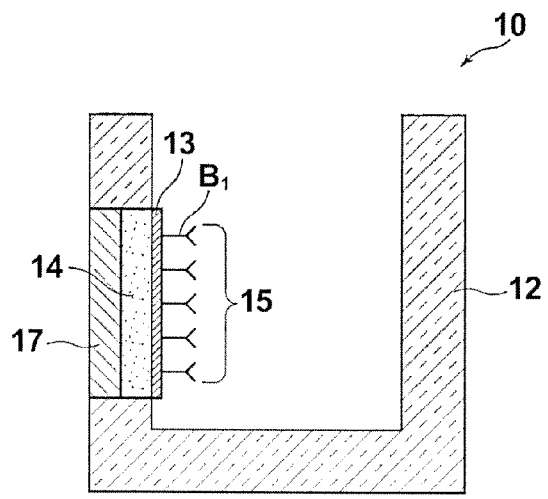

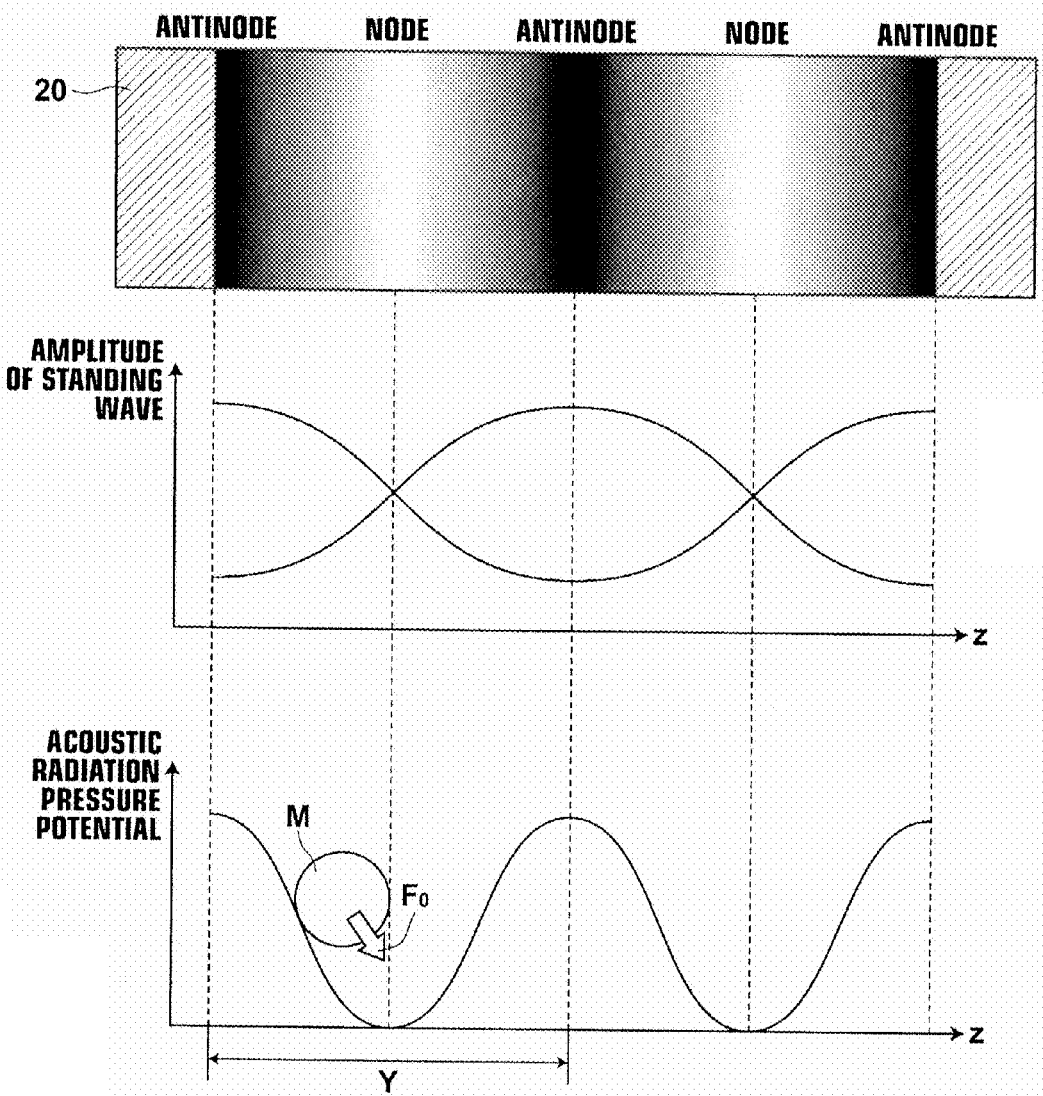

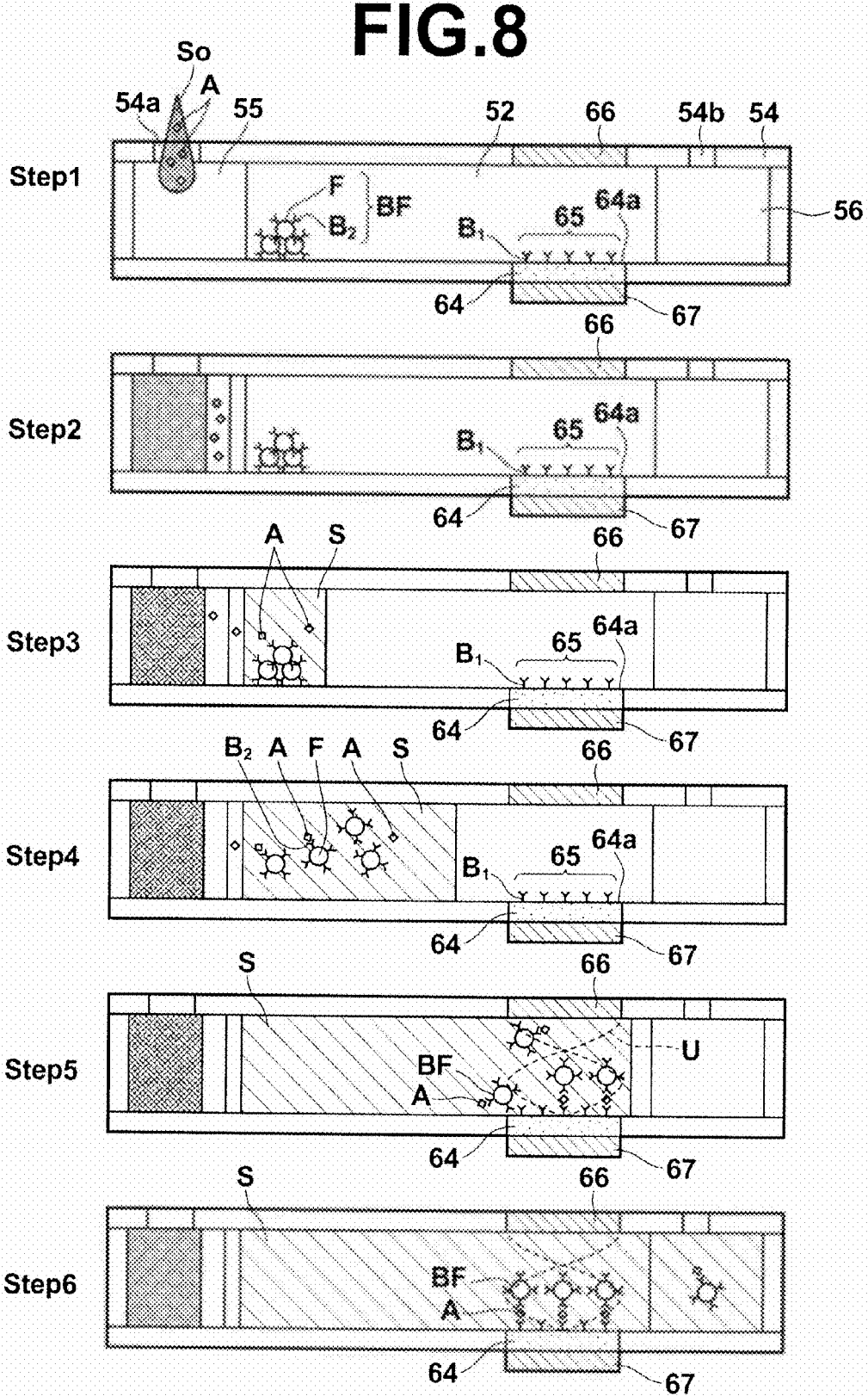

BIOLOGICAL SUBSTANCE ANALYZING METHOD, AND BIOLOGICAL SUBSTANCE ANALYZING CELL, BIOLOGICAL SUBSTANCE ANALYZING CHIP, AND BIOLOGICAL SUBSTANCE ANALYZING APPARATUS EMPLOYED IN THE BIOLOGICAL SUBSTANCE ANALYZING METHOD

BACKGROUND OF THE INVENTION

1. Field of the Invention

The present invention is related to a biological substance analyzing method, for detecting detection target substances within liquid samples with a sensor portion provided in a reaction chamber, and a biological substance analyzing cell, chip, and apparatus.

2. Description of the Related Art

Presently, analysis and quantification of biological substances such as sugars, proteins, and nucleic acids is being performed daily in a wide range of fields, such as clinical examinations, food inspection, and environmental inspections. There are various types of biological substance analysis and quantification methods according to the types of biological substances which are the targets of analysis and quantification. Some of these methods utilize reactions between biological substances and substances that have affinities for the biological substances. For example, quantification methods that utilize antigen antibody reactions are established as highly sensitive and reliable immunoassay methods, and are commonly used in a wide range of fields such as clinical examinations. However, if commercially available reagent kids are employed, each of the multitude of reactions take time, and expedient tests are difficult when there are great amounts of samples. This is because the kinetic energy at a specific temperature controls the reaction speed by the frequency at which molecules collide with each other.

Particularly in antigen antibody reactions in which one of the antigens and the antibodies are immobilized, the molecular collision frequency becomes extremely low, and the reaction speed also decreases correspondingly. Use of ultrasonic waves during reactions in order to increase reaction speeds has been described in U.S. Pat. No. 4,575,485, Japanese Unexamined Patent Publication No. 10(1998)-267927, and European Patent Publication No. 0767376, as a solution to resolve this issue. In this case, it is considered that the ultrasonic waves operate on the antigens or the antibodies which are not immobilized, to increase the collision frequency thereof with respect to the immobilized antibodies or antigens, to promote binding reactions.

U.S. Pat. No. 4,575,485 and Japanese Unexamined Patent Publication No. 10(1998)-267927 disclose inventions in which molecular vibrations are caused by ultrasonic waves to increase collision rates thereof with surrounding substances, thereby increasing reaction speeds. Further, the invention of Japanese Unexamined Patent Publication No. 10(1998)-267927 is characterized by modulating the frequency of the ultrasonic waves to disrupt the state of vibration, to cause translational movement over a wider range. European Patent Publication No. 0767376 discloses an invention that promotes antigen antibody reactions by applying minute voltages for short amounts of time (several tens of seconds or fifteen seconds) without causing electrolysis to occur in immune substances.

However, in the methods disclosed in U.S. Pat. No. 4,575,485 and Japanese Unexamined Patent Publication No. 10(1998)-267927, there is a problem that reaction speed is not improved when the concentration of immune substances is low even if the immune substances are caused to vibrate, because the amount of other immune substances in the vicinities thereof is low. In addition, in such low concentration situations, the amount of immune substance that can be detected at a sensor portion depends on the dispersion speed of the substance. Therefore, it is considered that a great improvement in detection sensitivity cannot be expected. Biological substances (such as blood, urine, and saliva) which are targets of immunodiagnosis commonly contain salt, and the electrical responsiveness of the substances themselves is high. Therefore, promotion of immune reactions using electrical fields may adversely affect these substances, and accordingly the method disclosed in European Patent Publication No. 0767376 is not favorable.

SUMMARY OF THE INVENTION

The present invention has been developed in view of the foregoing circumstances. It is an object of the present invention to provide a biological substance analyzing method that expedites and improves the efficiency of detection of detection target substances at a sensor portion, to enable accelerated analysis and measurement of the detection target substances with high sensitivity.

It is another object of the present invention to provide a biological substance analyzing cell, a biological substance analyzing chip, and a biological substance analyzing apparatus to be employed in the above biological substance analyzing method.

A biological substance analyzing method of the present invention employs a biological substance analyzing cell equipped with a reaction chamber having a sample supply space, an acoustic matching layer which is provided at a predetermined region of an inner wall of the reaction chamber that faces another inner wall, and a sensor portion provided within the reaction chamber, and is characterized by comprising:

supplying a liquid sample that includes a detection target substance into the sample supply space;

emitting ultrasonic waves such that a standing wave having a node positioned at the interface between the acoustic matching layer and the sample supply space is generated between the acoustic matching layer and the other inner wall of the reaction chamber;

concentrating the detection target substance at the interface by the capturing forces that operate in the direction of the nodes; and detecting the concentrated detection target substance with an immobilized binding substance, which is immobilized onto the sensor portion, that specifically binds with the detection target substance.

In the present specification, the expression "sample supply space" refers to a space formed by the reaction chamber, in which the liquid sample is stored and caused to contact the sensor portion. The expression "sample supply space" also refers to flow channels.

The "acoustic matching layer" refers to a layer having a material with an acoustic impedance equivalent to the acoustic impedance of the liquid sample which is supplied into the reaction chamber.

That a node is "positioned at the interface between the acoustic matching layer and the sample supply space" refers to a state in which a node of the standing waves is contained in the interface or in the vicinity of the interface. More specifically, the expression refers to a state in which a node of the standing waves is positioned within a range from $\lambda m/4$ toward the side of the acoustic matching layer from the interface to d/2 toward the side of the sample supply space from the interface. Note that λm is the wavelength of the ultrasonic waves at the acoustic matching layer, and d represents the particle size of labels which are utilized.

In the present specification, the "particle size" of the labels is the mode of the spherical diameters of the smallest sphere that circumscribes the particular labels. The mode of the spherical diameters is determined by using a Sysmex Zetasizer (Nano-ZS) to perform particle size measurements based on the dynamic light scattering method at a sample temperature of 25° C. The parameters which are set as measurement conditions are the refractive index of the particles and the refractive index of a solvent. For example, in the case that polystyrene particles are dispersed within plasma, the refractive index of polystyrene, 1.59, and the refractive index of plasma, 1.347, are employed as the parameters. The refractive index of the solvent is measured by a digital refractometer (ATAGO RX-5000α). Particle size measurements must be performed while the particles are in a dispersed state. Therefore, it is desirable for the particles to be dispersed within the actual sample liquid when performing measurements. This is so that the particles can be designed to maintain the dispersed state within the actual sample liquid. The particles may agglomerate in a solvent different from the actual sample liquid due to differences in pH and salt concentration, precluding accurate measurement of particle size. This is easily understood by those skilled in the art.

The expression "capturing forces that operate in the direction of the nodes" refers to the force that operates on substances within standing waves that causes the substances to be collected in the vicinity of the nearest node, based on the acoustic radiation pressure of the standing waves.

The expression "immobilized binding substance" refers to one of a pair of substances that specifically bind with each other, which is immobilized onto a cell (substrate). Note that the expression "pair of substances that specifically bind with each other" refer to pairs of substances that specifically discriminate each other and bind, such as antigens and antibodies, and proteins and cofactors.

A biological substance analyzing cell of the present invention comprises:

a reaction chamber that forms a sample supply space, into which liquid samples containing detection target substances are supplied;

an acoustic matching layer provided at a predetermined region of an inner wall of the reaction chamber that faces another inner wall; and a sensor portion provided on a surface of the acoustic matching layer toward the side of the sample supply space, on the surface of which an immobilized binding substance that specifically binds with the detection target substance is immobilized.

It is preferable for the biological substance analyzing cell of the present invention to further comprise:

a reflecting layer provided at the surface of the other inner wall of the reaction chamber that faces the acoustic matching layer so as to face the acoustic matching layer or on the surface of the acoustic matching layer opposite the side toward the sample supply space.

It is preferable for the sensor portion to have a dielectric layer and/or a metal layer.

A biological substance analyzing chip of the present invention comprises:

a flow channel member constituted by a flow channel through which liquid samples containing a detection target substance are caused to flow, a flow inlet connected to the flow channel for introducing the liquid samples into the flow channel, an air opening for causing the liquid samples which have been introduced into the flow channel to flow;

an acoustic matching layer that transmits ultrasonic waves, provided at a predetermined region on the inner wall of the flow channel member between the flow inlet and the air opening; and a sensor portion provided at the surface of the acoustic matching layer toward the side of the flow channel and/or at a position at a position on the surface of the inner wall of the flow channel shifted in the longitudinal direction of the flow channel from said surface of the acoustic matching layer;

an immobilized binding substance that specifically binds with the detection target substance being immobilized on the surface of the sensor portion.

In the present specification, that the sensor portion is "provided at the surface of the acoustic matching layer toward the side of the flow channel and/or at a position on the surface of the inner wall of the flow channel shifted in the longitudinal direction of the flow channel from said surface of the acoustic matching layer" includes cases in which the sensor portion is provided directly on the acoustic matching layer, the sensor portion is provided at a position on the surface of the inner wall of the flow channel shifted in the longitudinal direction of the flow channel from the acoustic matching layer, and the sensor portion is provided to straddle a position directly on the acoustic matching layer and the aforementioned shifted position. Note that the "longitudinal direction of the flow channel" refers to the direction along the flow channel, and the "position on the surface of the inner wall of the flow channel shifted in the longitudinal direction of the flow channel from the acoustic matching layer" refers to a position on the surface of the inner wall that molecules within the liquid sample will pass after passing through the vicinity of the acoustic matching layer, along with the flow of the liquid sample.

It is preferable for the biological substance analyzing chip of the present invention to further comprise:

a reflecting layer provided at the surface of the inner wall of the flow channel member that faces the acoustic matching layer so as to face the acoustic matching layer or on the surface of the acoustic matching layer opposite the side toward the flow channel.

It is preferable for the sensor portion to have a dielectric layer and/or a metal layer.

Further, it is preferable for the biological substance analyzing chip of the present invention to further comprise:

a label binding substance provided on the surface of the inner wall of the flow channel member upstream from the sensor portion;

the label binding substance being:

a first binding substance that specifically binds with the detection target substance or a second binding substance that competes with the detection target substance to specifically bind with the immobilized binding substance; and labeling particles modified with the first binding substance or the second binding substance.

Further, a biological substance analyzing apparatus of the present invention comprises:

the biological substance analyzing cell or the biological substance analyzing chip described above;

ultrasonic wave emitting means for emitting ultrasonic waves toward the interface between the acoustic matching layer and the sample supply space or the flow channel from a direction normal to the interface; and ultrasonic wave control means for controlling the ultrasonic wave emitting means such that a standing wave is generated on the interface and a node of the standing wave is positioned at the interface.

The biological substance analyzing method of the present invention emits and controls ultrasonic waves such that a node of the standing wave formed in the reaction chamber is positioned at the interface between the acoustic matching layer and the sample supply space. Therefore, it becomes possible to concentrate the detection target substance in the vicinity of the sensor portion by the capturing force that operates in the vicinity of the node. Thereby, expedient and highly efficient reactions are enabled between the detection target substance and the sensor portion. As a result, expedient and highly sensitive analysis and measurement becomes possible in biological substance analysis that detects detection target substances within liquid samples with a sensor portion provided in a reaction chamber.

The biological substance analyzing cell, the biological substance analyzing chip, and the biological substance analyzing apparatus of the present invention are equipped with the acoustic matching layer that transmits ultrasonic waves at a predetermined region within the sample supply space or the surface of the flow channel, such that the node of the standing wave formed in the reaction chamber is positioned at the interface of the acoustic matching layer and the reaction chamber. Therefore, it becomes possible to concentrate the detection target substance in the vicinity of the sensor portion by the capturing force that operates in the vicinity of the node. Thereby, expedient and highly efficient reactions are enabled between the detection target substance and the sensor portion. As a result, expedient and highly sensitive analysis and measurement becomes possible in biological substance analysis that detects detection target substances within liquid samples with a sensor portion provided in a reaction chamber or in a flow channel member.

BRIEF DESCRIPTION OF THE DRAWINGS

FIG. 2A is a schematic sectional diagram that illustrates how an acoustic matching layer is provided in a biological substance analyzing cell according to an embodiment of the present invention.

FIG. 2B is a schematic sectional diagram that illustrates how an acoustic matching layer is provided in a biological substance analyzing cell according to another embodiment of the present invention.

FIG. 2C is a schematic sectional diagram that illustrates how a metal layer is provided in a biological substance analyzing cell according to an embodiment of the present invention.

FIG. 5 is a graph that illustrates the relationships among standing waves, the amplitude of the standing waves, and acoustic radiation pressure potential.

FIG. 8 is a diagram that illustrates the steps of a biological substance analyzing method that employs a biological substance analyzing chip according to the second embodiment of the present invention.

DESCRIPTION OF THE PREFERRED EMBODIMENTS

Figure 1:
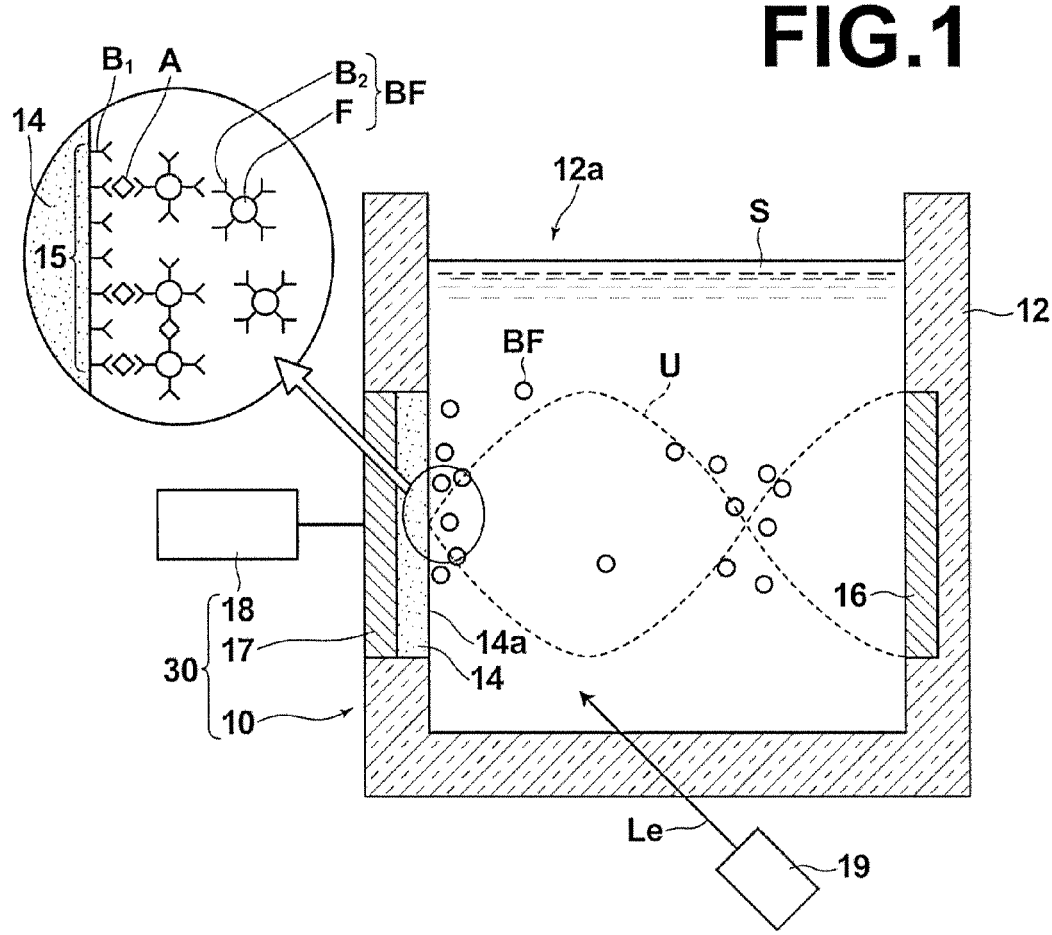
FIG. 1 is a schematic sectional diagram that illustrates a biological substance analyzing apparatus according to a first embodiment of the present invention.

Hereinafter, embodiments of the present invention will be described with reference to the attached drawings. However, the present invention is not limited to the embodiments to be described below. Note that the dimensions of the elements illustrated in the drawings may differ from the actual dimensions thereof, in order to facilitate visual recognition.

[First Embodiment of the Biological Substance Analyzing Method and the Biological Substance Analyzing Apparatus]

First, a biological substance analyzing method and a biological substance analyzing apparatus according to a first embodiment will be described. Note that the first embodiment will be described as a case in which antigens and antibodies are employed as pairs of substances that specifically bind with each other, the detection target substance is an antigen, the binding substance that specifically binds with the detection target substance is an antibody, and analysis is performed by the sandwich method that employs fluorescent labels.

The biological substance analyzing method of the first embodiment employs the biological substance analyzing apparatus 30 illustrated in FIG. 1. The biological substance analyzing apparatus 30 includes a biological substance analyzing cell 10 equipped with: a reaction chamber 12 that forms a sample supply space 12a; an acoustic matching layer 14 provided at a predetermined region of an inner wall of the reaction chamber 12 that faces another inner wall; a reflecting layer 16 provided on the surface of the inner wall of the reaction chamber 12 that faces the acoustic matching layer 14; and a sensor portion 15 provided on a surface of the acoustic matching layer 14 toward the side of the sample supply space 12a. A liquid sample S that includes antigens A, which have fluorescent labels, is supplied into the sample supply space 12a. Ultrasonic waves are emitted such that a standing wave U having a node positioned at the interface (matching interface 14a) between the acoustic matching layer 14 and the sample supply space 12a is generated between the acoustic matching layer 14 and the inner wall of the reaction chamber 12 that faces the acoustic matching layer 14. The antigens A are concentrated at the matching interface 14a by capturing forces that operate in the direction of the nodes. The concentrated antigens A are immobilized onto the sensor portion 15 by immobilized antibodies B1 which are immobilized on the sensor portion 15. Fluorescent signals from the fluorescent labels on the immobilized antigens A are detected, to analyze the presence or absence and/or the amount of the antigens A.

The method by which the antigens A are fluorescently labeled is not particularly limited, and fluorescent pigment, quantum dots, etc. may be employed. Labeling antibodies BF (label binding substance), constituted by a first binding substance that specifically binds with the antigens A (detection target substance) or a second binding substance that competes with the antigens A (detection target substance) to specifically bind with the immobilized antibodies B1 (immobilized binding substance) and labeling particles modified with the first binding substance or the second binding substance are preferable as labels for the antigens A. It is possible for the labeling particles (for example, polystyrene particles) to envelop a plurality of fluorescent pigment molecules, quantum dots, etc. in the interiors thereof, which enables analysis to be performed with high sensitivity. It is preferable for the size of the labeling particles to be within a range from 0.05 μm to 10 mm, and more preferably 0.1 μm to 1 mm, because the capturing forces of standing waves is proportionate to the volumes of substances during concentration by ultrasonic waves, and from the viewpoint of dispersion speed. Accordingly, in the case that the immune substances to be handled are smaller than the labeling particles, or if reaction speed is to be further accelerated, it is necessary to modify the labeling particles of this size with one of the immune substances to perform immune measurements. In the first embodiment that employs the sandwich method, the labeling antibodies BF are constituted by first antibodies 32 and fluorescent particles F having a plurality of fluorescent pigment molecules enveloped therein and of which the surfaces are modified with the first antibodies 132. In addition, the timing at which the antigens A are labeled is not particularly limited. The antigens A may be caused to react with the labels prior to the liquid sample S being supplied into the sample supply space 12a, or may be caused to react with the labels after the liquid sample S is supplied into the sample supply space 12a.

Detection of the fluorescent signals is performed by a light source 19 irradiating the sensor portion 15 with excitation light Le to cause fluorescence to be generated by the labeling antibodies BF, and by detecting the fluorescence visually or with a photodetector.

In greater detail, the biological substance analyzing apparatus 30 of FIG. 1 is equipped with: the biological substance analyzing cell 10 comprising the reaction chamber 12 that forms the sample supply space 12a, the acoustic matching layer 14 provided at a predetermined region of an inner wall of the reaction chamber 12 that faces another inner wall, and the sensor portion 15 provided within the reaction chamber 12; an ultrasonic wave emitting means 17 for emitting ultrasonic waves toward the interface (matching interface 14a) between the acoustic matching layer 14 and the sample supply space 12a from a direction normal to the matching interface 14a; and ultrasonic wave control means 18 for controlling the ultrasonic wave emitting means 17 such that the standing wave U is generated on the matching interface 14a and a node of the standing wave U is positioned at the matching interface 14a.

The biological substance analyzing cell 10 is equipped with: the reaction chamber 12 that forms the sample supply space 12a; the acoustic matching layer 14; the reflecting layer 16; and the sensor portion 15. The shape of the cell 10 is not particularly limited, and commonly utilized cubic cells, cylindrical cells, etc., may be employed. In addition, the biological substance analyzing cell 10 may be a biological substance analyzing chip, in which the shape of the sample supply space 12a thereof is that of a flow channel. Embodiments that employ biological substance analyzing chips will be described as a second and a third embodiment of the present invention.

The acoustic matching layer 14 is a layer that functions to match the acoustic impedance ($Z$: $Z=c$ (speed of sound within a substance)$\times\rho$ (the density of the substance)) of the inner wall of the reaction chamber 12 and the liquid sample S which is supplied into the sample supply space 12a. Therefore, the acoustic matching layer 14 is formed by a material with an acoustic impedance equivalent to the acoustic impedance of the liquid sample S. The material of the acoustic matching layer 14 is not particularly limited. The liquid sample S in cases that biological substances are analyzed is commonly water ($Z=1.48\times10^6$ N·s·m$^{-3}$ (at room temperature)). Therefore, dielectric materials such as polymers may be employed as the material of the acoustic matching layer 14. Soft polyethylene ($Z=1.75\times10^6$ N·s·m$^{-3}$ (at room temperature)) and rubber materials are preferable. Silicone rubbers such as PDMS (polydimethylsiloxane), natural rubber ($Z=1.50\times10^6$ N·s·m$^{-3}$ (at room temperature)), and styrene-butadiene rubber ($Z=1.76\times10^6$ N·s·m$^{-3}$ (at room temperature)) are more preferable. PDMS ($Z=1.06\times10^6$ N·s·m$^{-3}$ (at room temperature)) is particularly preferable, from the viewpoint of ease in shaping and controlling the thickness of the layer.

The acoustic matching layer 14 is provided at the predetermined region of the inner wall of the reaction chamber 12 of the biological substance analyzing cell 10 such that the surface thereof appears in the sample supply space 12a. That is, the acoustic matching layer 14 is provided such that the surface thereof contacts the liquid sample S which is supplied into the sample supply space 12a, and such that it faces another inner wall of the reaction chamber 12. Thereby, repeated reflection of the ultrasonic waves between the acoustic matching layer 14 and the inner wall that faces it becomes possible, and generation of the standing wave U therebetween is enabled. The liquid sample S and the acoustic matching layer 14 are acoustically matched at this time. Therefore, it becomes possible to position a node of the standing wave U at the interface (matching interface 14a) between the acoustic matching layer 14 and the sample supply space 12a (or the liquid sample S). The nodes of the standing wave U will be described in detail later. For example, in the case that in the case that the cell is a cubic cell or a cylindrical cell, the acoustic matching layer 14 may be provided on the side wall portion thereof. The acoustic matching layer 14 may be formed to be embedded into an inner wall of the reaction chamber 12 as illustrated in FIG. 2A, or formed on the surface of an inner wall of the reaction chamber 12 as illustrated in FIG. 2B. In the case that the acoustic matching layer is provided as illustrated in FIG. 2B, the ultrasonic waves are emitted onto the acoustic matching layer 14 via the reaction chamber 12.

The sensor portion 15 is a region on the acoustic matching layer 14, on which the immobilized antibodies 31 for detecting the antigens A are immobilized. A single sensor portion 15 or a plurality of sensor portions 15 may be provided. In the case that a plurality of sensor regions 15 having different types of immobilized antibodies immobilized thereon are provided, a plurality of types of antigens can be detected, and therefore, multiple item array analysis and measurement becomes possible. The immobilized antibodies B1 are antibodies that specifically bind with the antigens A. The type of antibody is not particularly limited, and may be selected according to detection conditions (particularly the type of antigen the antigen A is). For example, in the case that the antigens A are hCG antigens (molecular weight: 38,000 Da), monoclonal antibodies that specifically bind with the antigens A may be employed as the immobilized antibodies 131. Examples of methods by which the immobilized antibodies B1 may be immobilized onto acoustic matching layer 14 include physical adsorption, and immobilization by static electricity or by chemical bonds after introducing functional groups such as carboxyl groups, amino groups, and thiol groups onto the acoustic matching layer by surface modifications. An example of a chemical binding method is the amine coupling method, in which carboxyl groups are provided on the acoustic matching layer 14 then activated, and caused to bind with the amino groups of the antibodies.

The sensor portion 15 may be configured to be equipped with a dielectric layer 13 and/or a metal layer, as illustrated in FIG. 2C. In the case that the dielectric layer 13 is provided on the surface of the acoustic matching layer 14, the dielectric layer 13 may be employed as an immobilizing layer on which immune substances (antibodies, for example) are immobilized, in cases that it is difficult to immobilize these substances on the acoustic matching layer 14. In the case that the metal layer is provided to contact the surface of the acoustic matching layer 14, a high sensitivity analyzing method that utilizes plasmon generated in the metal layer can also be utilized. For example, in the case that the metal layer is a film formed by metallic material, the surface plasmon resonance method, the surface plasmon enhanced fluorometry method, or the SPCE (Surface Plasmon Coupled Emission) method may be utilized. In the case that the metal layer is a layer formed by fine metal particles, the local surface plasmon resonance method may also be utilized. However, in the case that the dielectric layer 13 and/or the metal layer is provided to contact the surface of the acoustic matching layer 14, it is necessary to employ the aforementioned materials that have acoustic matching functions as the material of the dielectric layer 13, and to form the metal layer to be thin, so as not to influence the acoustic matching function of the acoustic matching layer 14.

The reflecting layer 16 is provided to face the acoustic matching layer 14 to efficiently reflect the ultrasonic waves (that is, to efficiently cause the standing wave U to be generated). It is preferable for a material that has an acoustic impedance which is greatly different from that of the liquid sample (water), in order to increase the reflectance with respect to ultrasonic waves. Examples of such materials include dielectrics such as glass, and metals such as aluminum. The reflecting layer 16 may be embedded into an inner wall of the reaction chamber 12 or formed on the surface of an inner wall of the reaction chamber 12 in the same manner as the acoustic matching layer 14.

Figure 3A:
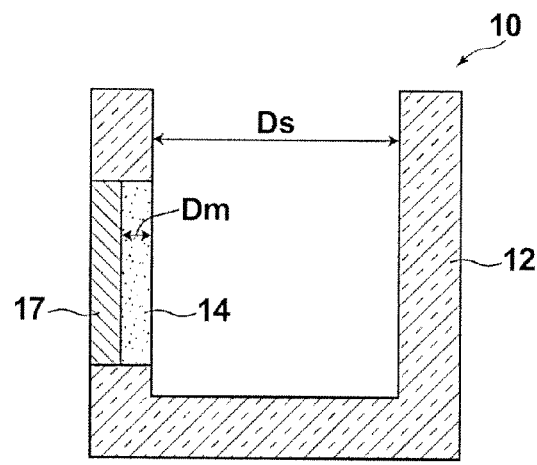
FIG. 3A is a schematic sectional diagram that illustrates the positional relationships among an acoustic matching layer, a reflecting layer, and a sample supply space in a biological substance analyzing cell according to an embodiment of the present invention.
Figure 3B:
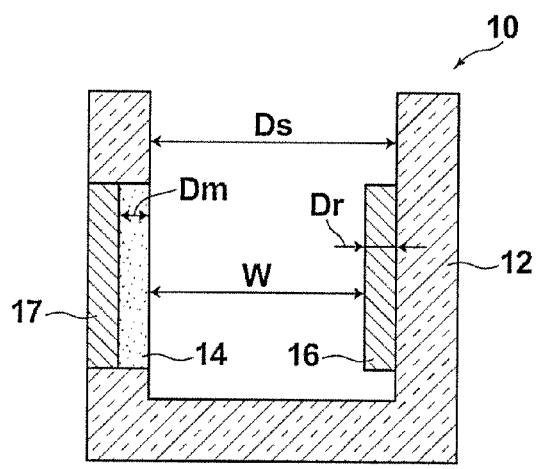
FIG. 3B is a schematic sectional diagram that illustrates the positional relationships among an acoustic matching layer, a reflecting layer, and a sample supply space in a biological substance analyzing cell according to another embodiment of the present invention.
Figure 3C:
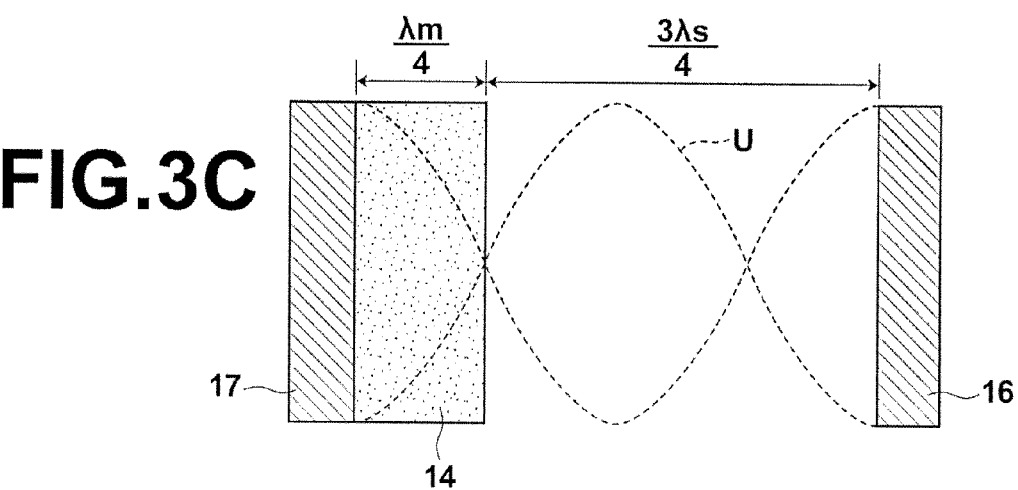
FIG. 3C is a schematic sectional diagram that illustrates the positional relationship between an interface between an acoustic matching layer and a sample supply space, and the nodes of a standing wave in a biological substance analyzing cell according to an embodiment of the present invention.

The thickness Dm of the acoustic matching layer 14, the thickness Dr of the reflecting layer 16, and the distance Ds from the matching interface 14a to the inner wall that it faces are designed appropriately such that a node of the standing wave U is positioned at the matching interface 14a, that is, such that the matching interface 14a is perpendicular to the propagating direction of the ultrasonic waves and includes a node of the standing wave U. In the case that the reflecting layer 16 is not provided, it is preferable for the thickness Dm of the acoustic matching layer 14 and the distance Ds to be odd multiples of ¼ the wavelengths $\lambda m$ and $\lambda s$ of the ultrasonic waves therein, as illustrated in FIG. 3A. Particularly, it is preferable for the thickness Dm to be $\lambda m/4$ and for the distance Ds to be $\lambda s/4$. Meanwhile, in the case that the reflecting layer 16 is provided, it is preferable for the thickness Dm of the acoustic matching layer 14 and the distance W from the matching interface 14a to the reflecting layer 16 (the effective width of the sample supply space W=Ds−Dr) to be odd multiples of ¼ the wavelengths $\lambda m$ and $\lambda s$ of the ultrasonic waves therein, as illustrated in FIG. 3B. Particularly, it is preferable for the thickness Dm to be $\lambda m/4$ and for the distance W to be $\lambda s/4$. For example, in the case that the reflecting layer 16 is provided and the thickness Dm of the acoustic matching layer 14 is $\lambda m/4$ and the effective width W of the sample supply space is $3\lambda s/4$, a standing wave U such as that illustrated in FIG. 3C is generated between the ultrasonic wave emitting means 17 and the reflecting layer 16.

Figure 4A:
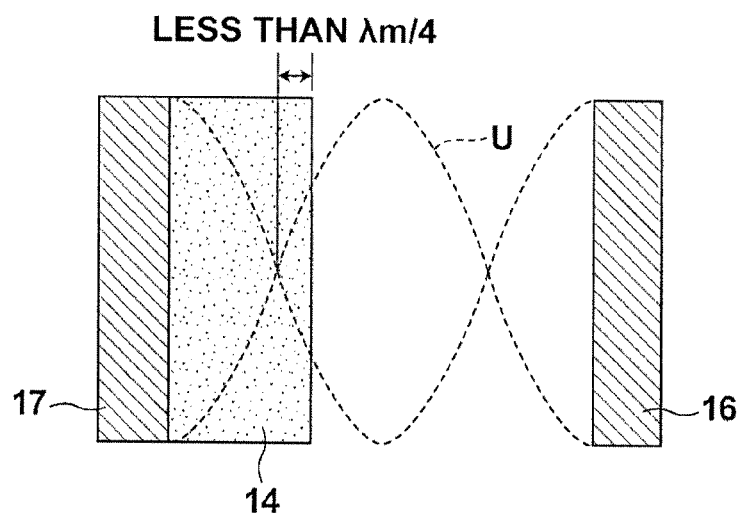
FIG. 4A is a schematic sectional diagram that illustrates a state in which the position of a node of a standing wave is shifted from the interface between an acoustic matching layer and a sample supply space toward the interior of the acoustic matching layer.
Figure 4B:
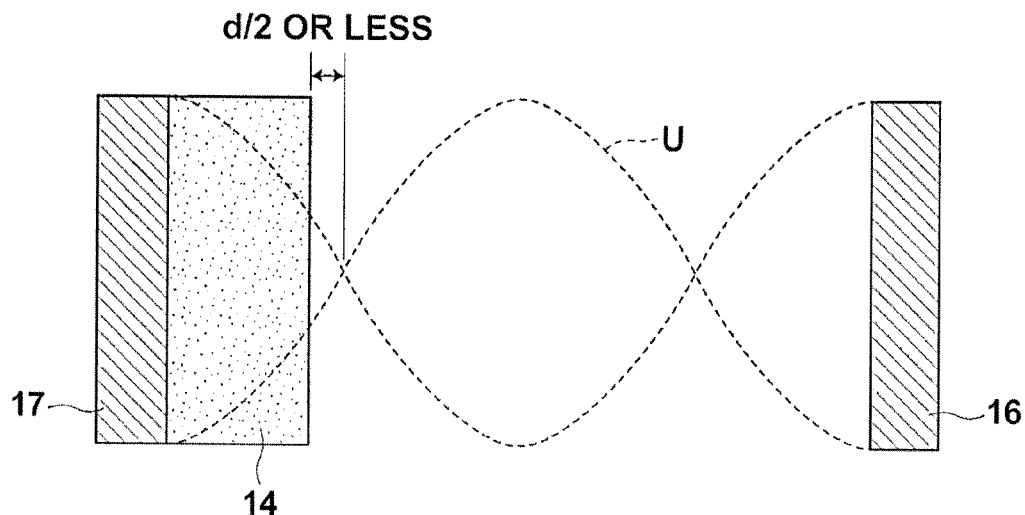
FIG. 4B is a schematic sectional diagram that illustrates a state in which the position of a node of a standing wave is shifted from the interface between an acoustic matching layer and a sample supply space toward the sample supply space.

In the present invention, capturing forces act onto substances in the vicinities of nodes such that the substances are concentrated at the nodes. Therefore, it is not necessary for the matching interface 14a to be provided such that it is perpendicular to the propagating direction of the ultrasonic waves and includes a node of the standing wave U. That is, in the case that the position of a node is shifted from the matching interface 14a toward the interior of the acoustic matching layer 14, and the amount of shifting is less than $\lambda m/4$, substances in the vicinity of the node are moved by the capturing forces that work from an antinode toward the node, and therefore are concentrated on the matching interface 14a, as illustrated in FIG. 4A. In addition, in the case that the position of a node is shifted from the matching interface 14a toward the side of the sample supply space 12a, and the amount of shifting is within d/2 (d is the particle size of labels which are utilized), the detection target substance can be detected at the sensor portion 15 due to Brownian motion within liquids and electrical attraction between the detection target substance and the immobilized binding substance, to improve reaction speeds to a degree. Accordingly, in the present specification, that the "node of the standing wave U is positioned at the interface (matching interface 14a) between the acoustic matching layer 14 and the sample supply space 12" refers to a state in which a node of the standing waves is positioned within a range from $\lambda m/4$ toward the side of the acoustic matching layer from the interface to d/2 toward the side of the sample supply space from the interface.

The number of nodes of the standing wave U is not particularly limited. However, it is preferable for a single node to be present within the sample supply space 12 in order to efficiently concentrate the antigens A at the sensor portion 15.

The ultrasonic wave emitting means 17 is an ultrasonic wave transducer, for example. Ultrasonic wave transducers are piezoelectric elements formed by piezoelectric ceramics, or by polymeric molecular films such as polyvinyl pyrolidone. PZT-Pb (Zr.Ti) O3 type Soft Material C-82 (by Fuji Ceramics) is a preferred ultrasonic wave transducer. In addition, the ultrasonic wave transducer may be a single transducer or an array transducer. It is preferable for the resonant frequency to be within a range from 100 kHz to 100 MHz. A resonant frequency of approximately 3 MHz is particularly preferred. The ultrasonic wave emitting means 17 may be in direct contact with the liquid sample S within the flow channel. However, taking the fact that the apparatus will be used repeatedly into consideration, it is preferable for the ultrasonic wave emitting means 17 to emit ultrasonic waves into the sample supply space 12a via the reaction chamber 12 or the acoustic matching layer 14 (refer to FIGS. 2A through 2C).

The ultrasonic wave control means 18 controls the ultrasonic wave emitting means 17 such that the standing wave U is generated on the matching interface 14a and a node of the standing wave U is positioned at the matching interface 14a. The control of the ultrasonic wave emitting means 17 is to make fine adjustments based on specific individual analysis results when generating the standing wave U. The ultrasonic wave control means 18 may be a separate unit equipped with a power source, an ultrasonic wave generating circuit, a modulating circuit, and an output circuit. In addition, the ultrasonic wave control means 18 may be further equipped with additional circuits, such as a circuit for freely forming the waveform of the ultrasonic waves as necessary. A multi-function generator WF1974 (by NF Corporation) may be employed as the ultrasonic wave control means 18, for example. The waveform of the drive voltage may be any desired shape, such as a sine wave, a rectangular wave, a triangular wave, and a ramp wave.

Hereinafter, the biological substance analyzing method and the operation of the biological substance analyzing apparatus 30 of the first embodiment will be described.

In an assay method, in which one substance (antibodies B1) of a pair of immune substances (substances that specifically bind with each other) is immobilized onto the two dimensional sensor portion 15, the specific properties of the reactions are utilized to detect the other substance (antigens A) of the pair of immune substance, to qualitatively or quantitatively analyze the amount of the other substance (antigens A), the speed of the aforementioned reactions is expressed by the Langmuir adsorption formula shown below.

$$\frac{d\theta}{dt} = k_a C(1-\theta) - k_d \theta \quad \text{Formula (1)}$$

wherein $\theta$ is the percentage of the number of sites (number of immobilized antibodies 131 which have bound with the antigens A) that the antigen A (detection target substance) have bound to, with respect to the number of sites (number of immobilized antibodies 31) which are capable of binding with the antigens A (detection target substance) on the sensor portion 15. That is, $\theta$ represents the percentage of the sensor portion 15 occupied by the antigens A. $k_a$ and $k_d$ respectively represent a binding speed coefficient and a disassociation speed constant, which depend on the immune substances (the pair of substances that specifically bind with each other). C represents the concentration of the antigens A (detection target substance) within the liquid sample.

In the assay method described above, improving reaction speeds refers to increasing the value of $d\theta/dt$. If the constant $k_a$ is increased and the constant $k_d$ is decreased in the formula above, the reaction speed can be improved. However, these constants are determined by the immune substances that react with each other, and therefore are physical quantities that cannot be improved after selecting the immune substances. Meanwhile, as the antigens A bind to the sensor portion 15, the concentration C of the antigens within the liquid sample S decreases. Therefore $d\theta/dt$, and consequently, the reaction speed, decreases. If the liquid sample S is supplied before the concentration C decreases due to the aforementioned binding by causing the liquid sample S to flow through a flow channel or the like, the decrease in concentration can be prevented, and reaction speed can be maintained. That is, the reaction speed being controlled by dispersion can be prevented by causing the liquid sample S to flow. However, even if the reaction speed being controlled by dispersion can be prevented, the reaction speed is determined by the antigen concentration C of the supplied liquid sample S, and therefore, further improvements in reaction speed cannot be expected. Therefore, the present invention emits the ultrasonic waves into the sample supply space 12a such that a node of the standing wave U is positioned at the matching interface 14a. Thereby, the antigens A are quickly and efficiently transported onto the sensor portion 15 by the capturing forces that operate on substances in the vicinity of the node. The antigens A become concentrated on the sensor portion 15, to effectively increase the antigen concentration C. Thereby, the percentage of occupation $\theta$ is greatly increased within a short period of time even if a liquid sample S having a low antigen concentration C is employed, and signals sufficiently greater than noise signals, such as apparatus noise including dark current, can be detected. Accordingly, expedient analysis and measurement at high sensitivity can be achieved.

The capturing forces are forces that operate toward the nearest node. The intensity $F_0$ of the capturing forces is proportionate to the volume V of a substance M, the frequency f of a sound wave, etc., as shown in Formula (2) below.

$$F_0(z) = \frac{5\pi}{4\rho_0 c_0^3} V P_0^2 f \sin\left(2\pi \frac{z}{\lambda/2}\right) \quad \text{Formula (2)}$$

wherein $F_0$ represents the intensity of the capturing forces, z represents the distance from the end of the standing wave U as illustrated in FIG. 5, $\rho_0$ the density of a medium, $c_0$ represents the speed of sound in a medium, V represents the volume of a substance M, $P_0$ represents acoustic pressure, f represents the frequency of the standing wave, and $\lambda$ represents the wavelength of the standing wave. Element 20 of FIG. 5 denotes a fixed end of the standing wave U. Alternatively, the intensity of the capturing forces may be said to be proportionate to the acoustic radiation pressure potential curve illustrated in FIG. 5. Accordingly, the capturing force intensity $F_0$ becomes greater for substances close to the position of an antinode of the standing wave U, whereas substances in the vicinity of a node are not moved much. Here, the acoustic radiation pressure potential refers to the mechanical potential within the acoustic field of the standing wave.

In addition, the size of a capturing space Y within which the substance M is captured by the capturing forces is approximately half the wavelength of the ultrasonic waves. Here, the "capturing space" is a space having the position of a node of the standing wave U at its center, and is a range within which the capturing forces that operate on substances present within the standing wave U can capture a substance and move the substance toward a specific node. The capturing forces are forces that operate on substances within standing waves that cause the substances to be collected in the vicinity of the nearest node, based on the acoustic radiation pressure of the standing waves. That is, the capturing space may be considered to be a range from a position corresponding to a local maximum to a position corresponding to an adjacent local maximum of acoustic radiation pressure potential (indicated by Y in FIG. 5), on which the capturing forces are based. For example, in the case that the frequency of the ultrasonic waves is 1 MHz, the wavelength $\lambda$ thereof is 1.5 mm, based on the speed of sound in distilled water. Accordingly, the size of the capturing space Y in this case will be 750 μm. This also means that the size of the capturing space Y can be continuously varied by sweeping the frequency of the ultrasonic waves.

In assays performed according to the sandwich method, in the case that the antigens A are labeled prior to being immobilized onto the sensor portion 15, reactions are divided into two steps. The first step includes primary reactions, in which the antigens A are caused to react with the labeling antibodies BF, and the second step includes secondary reactions, in which the combinations of the labeling antibodies BF and the antigens A are caused to react with the immobilized antibodies B1. Because the primary reactions are performed between the antigens A and the labeling antibodies BF within the liquid sample S, which has a sufficiently high concentration of the labeling antibodies BF, the reaction efficiency is favorable, and approximately 90% or more of the antigens A bind with the labeling antibodies BF within a short amount of time. In contrast, the secondary reactions are reactions between the antigens A of the aforementioned combinations within the liquid sample S and the immobilized antibodies B1 on the two dimensional planar sensor portion 15, the reaction efficiency is low, and the binding rate is several % or less. For this reason, it is extremely important to improve the reaction efficiency of the secondary reactions. The transport and concentration of the combinations (the antigens A) on the sensor portion 15 realized by the present invention exhibits extremely great advantageous effects. In the case that the distance Ds from the matching interface 14*a* to the inner wall that faces the matching interface 14*a* (or the effective width W of the sample supply space) is $3\lambda s/4$, two nodes will be formed within the sample supply space 12*a* (refer to FIG. 3C). In this case, the combinations (antigens A) will be concentrated in the vicinity of the sensor portion 15 and at a position $\lambda s/2$ away from the sensor portion 15. The combinations (antigens A) which are concentrated at the position away from the sensor portion 15 cannot bind with the immobilized antibodies B1 on the sensor portion 15, and do not contribute to the reactions on the sensor portion. However, because the reaction efficiency of the secondary reactions is extremely low, on the order of several % or less, the concentration of the combinations (antigens A) in the vicinity of the sensor portion 15 will sufficiently improve the reaction speed among the combinations (antigens A) and the immobilized antibodies B1.

As described above, the biological substance analyzing method of the first embodiment emits and controls ultrasonic waves such that a node of the standing wave U formed in the reaction chamber 12 is positioned at the interface (matching interface 14*a*) between the acoustic matching layer 14 and the sample supply space 12*a*. Therefore, it becomes possible to concentrate the detection target substance in the vicinity of the sensor portion 15 by the capturing force that operates in the vicinity of the node. Thereby, expedient and highly efficient reactions are enabled between the detection target substance and the sensor portion 15. As a result, expedient and highly sensitive analysis and measurement becomes possible in biological substance analysis that detects detection target substances within the liquid sample S with the sensor portion 15 provided in the reaction chamber 12.

The biological substance analyzing cell 10 and the biological substance analyzing apparatus 30 of the first embodiment are equipped with the acoustic matching layer 14 that transmits ultrasonic waves at a predetermined region within the sample supply space 12*a*, such that the node of the standing wave U formed in the reaction chamber 12 is positioned at the matching interface 14*a*. Therefore, it becomes possible to concentrate the detection target substance in the vicinity of the sensor portion 15 by the capturing force that operates in the vicinity of the node. Thereby, expedient and highly efficient reactions are enabled between the detection target substance and the sensor portion 15. As a result, expedient and highly sensitive analysis and measurement becomes possible in biological substance analysis that detects detection target substances within the liquid sample S with the sensor portion 15 provided in the reaction chamber 12.

(Design Modifications to the First Embodiment)

In the embodiment described above, fluorescent labels are employed as the labels for the antigens A. Alternatively, other photoresponsive labels (such as phosphorous labels, and scattered light labels) may be employed as the labels. In addition, the biological substance analyzing method and the biological substance analyzing apparatus of the first embodiment may be combined with various other types of immune measurement methods, such as the radioimmunoassay method (RTA) that employs radioactive isotopes, the enzyme immunoassay method (EIA) that employs enzymes, and the chemiluminescent enzyme immunoassay method (CLEIA).

Figure 6:
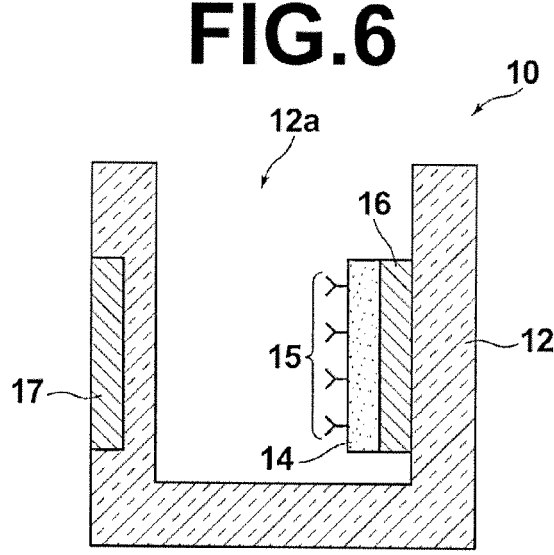
FIG. 6 is a schematic sectional diagram that illustrates how an acoustic matching layer is provided in a biological substance analyzing cell according to still another embodiment of the present invention.

In addition, the acoustic matching layer 14 may be provided toward the side of the reflecting layer 16, as illustrated in FIG. 6. In this case, the sensor portion 15 will be on the surface of the acoustic matching layer 14. Further, the acoustic matching layer 14 may be provided on both the side toward the ultrasonic wave emitting means 17 and the side toward the reflecting layer 16. In this case, the sensor portion 15 may be provided on one or both of the acoustic matching layers 14.

[Second Embodiment of the Biological Substance Analyzing Method and the Biological Substance Analyzing Apparatus]

Next, a biological substance analyzing method and a biological substance analyzing apparatus according to a second embodiment will be described. Note that the second embodiment will also be described as a case in which antigens and antibodies are employed as pairs of substances that specifically bind with each other, the detection target substance is an antigen, the binding substance that specifically binds with the detection target substance is an antibody, and analysis is performed by the sandwich method that employs fluorescent labels. Note that elements which are the same as those of the first embodiment will be denoted with the same reference numerals, and detailed descriptions thereof will be omitted insofar as they are not particularly necessary.

Figure 7A:
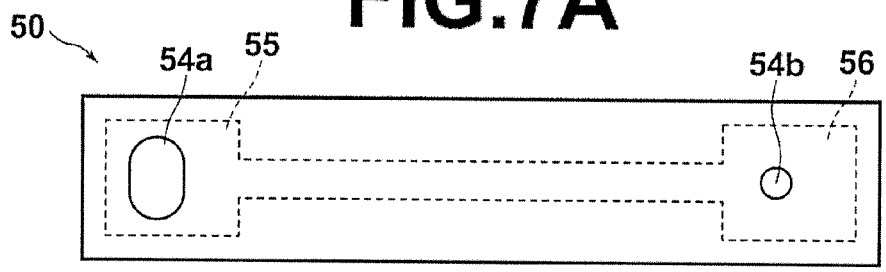
FIG. 7A is a schematic plan view that illustrates a biological substance analyzing apparatus according to a second embodiment of the present invention.
Figure 7B:
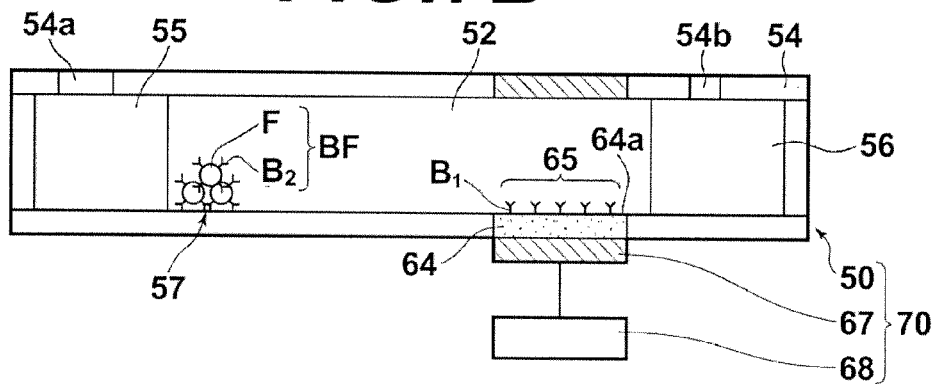
FIG. 7B is a schematic sectional diagram that illustrates a biological substance analyzing apparatus according to a second embodiment of the present invention.

The biological substance analyzing method of the second embodiment employs a biological substance analyzing apparatus 70 illustrated in FIGS. 7A and 7B. The biological substance analyzing apparatus 70 includes a biological substance analyzing chip 50 equipped with a flow channel member 54 that forms a channel 52 for the liquid sample S that includes the antigens A to flow through, a flow inlet 54*a*, and an air opening 54*b*. An acoustic matching layer 64 and a sensor portion 65 are provided at a predetermined region of an inner wall of the flow channel member 54. The liquid sample S that includes antigens A, which have fluorescent labels, is supplied into the flow channel 52. Ultrasonic waves are emitted such that a standing wave U having a node positioned at the interface (matching interface 64*a*) between the acoustic matching layer 64 and the flow channel 52 is generated between the acoustic matching layer 64 and the inner wall of the flow channel member 54 that faces the acoustic matching layer 64. The antigens A are concentrated at the matching interface 64*a* by capturing forces that operate in the direction of the nodes. The concentrated antigens A are immobilized onto the sensor portion 65 by immobilized antibodies 31 which are immobilized on the sensor portion 65. Fluorescent signals from the fluorescent labels on the immobilized antigens A are detected, to analyze the presence or absence and/or the amount of the antigens A.

In greater detail, the biological substance analyzing apparatus 70 of FIGS. 7A and 7B is equipped with: the biological substance analyzing chip 50; an ultrasonic wave emitting means 67 for emitting ultrasonic waves toward the matching interface 64a from a direction normal to the matching interface 64a; and ultrasonic wave control means 68 for controlling the ultrasonic wave emitting means 67 such that the standing wave U is generated on the matching interface 64a and a node of the standing wave U is positioned at the matching interface 64a.

The biological substance analyzing chip 50 is equipped with the flow channel member 54 that forms the flow channel 52, through which the liquid sample that includes the antigens A is caused to flow, the flow inlet 54a connected to the flow channel, through which the liquid sample S is injected, and the air opening 54b that causes the liquid sample S to flow through the channel 52, as illustrated in FIGS. 7A and 7B. The acoustic matching layer 64 that transmits ultrasonic waves is provided at a predetermined region on the inner wall of the flow channel member 54 between the flow inlet 54a and the air opening 54b. The sensor portion 65 provided on the surface of the acoustic matching layer 64 toward the side of the flow channel 52 and/or at a position on the surface of the inner wall of the flow channel 52 shifted in the longitudinal direction of the flow channel 52 from said surface of the acoustic matching layer 64. The immobilized antibodies 31 that specifically bind with the antigens A are immobilized on the surface of the sensor portion 65.

In addition, a predetermined region (labeling antibody adsorption area 57), at which the labeling antibodies BF, constituted by the antibodies B2 and fluorescent particles F of which the surfaces are modified with the antibodies B2, are physically adsorbed, is provided toward the upstream side of the flow channel 52. This configuration obviates a separate operation to label the antigens.

The flow channel member 54 is preferably formed by resin. In the case that the flow channel member 54 is formed by resin, polymethyl methacrylate (PMMA), polycarbonate (PC), and non crystalline polyolefin (APO) that includes cycloolefin are particularly preferred.

The acoustic matching layer 64, a reflecting layer 66, a dielectric layer, a metal layer, the ultrasonic wave emitting means 67 and the ultrasonic wave control means 68 are the same as those of the first embodiment.

In the second embodiment, the sensor portion 65 is provided on the surface of the acoustic matching layer 64 toward the side of the flow channel 52.

The procedures by which an assay is performed according to the sandwich method to detect whether the antigen A, which is a detection target substance, is included in blood (whole blood) by the biological substance analyzing method of the second embodiment using the biological substance analyzing chip 50 will be described with reference to FIG. 8.

Step 1: The blood So (whole blood), which is the target of inspection, is injected through the flow inlet 54a. Here, a case will be described in which the blood So includes the antigen A to be detected. In FIG. 8, the blood So is represented by the cross hatched regions.

Step 2: The blood So is filtered by a membrane filter 55, and large molecules, such as red blood cells and white blood cells, are separated as residue.

Step 3: Plasma S (the blood from which blood cells have been filtered out by the membrane filter 55) leaks out into the channel 52 by capillary action. Alternatively, in order to expedite reactions and to shorten detection time, a pump may be connected to the air opening 54b, and the plasma S may be caused to flow by suctioning and extruding operations of the pump. In FIG. 8, the plasma S is represented by the hatched regions.

Step 4: the plasma S, which has leaked into the channel 52 and the labeling antibodies BF (the fluorescent particles F modified with the antibodies B2), which are provided within the channel 52, mix, and the antigens A within the plasma S bind with the labeling secondary antibodies BF.

Step 5: the plasma S gradually flows along the channel 52 toward the air opening 54b, and the antigens A, which are bonded to the labeling secondary antibodies BF, bind with the immobilized antibodies B1, which are immobilized onto the sensor portion 65. So called sandwich configurations, in which the antigens A are sandwiched between the immobilized antibodies 31 and the labeling antibodies BF, are formed. At this time, ultrasonic waves are emitted to generate a standing wave U having a node positioned at the matching interface 64a, to cause the antigens A to be concentrated at the matching interface 64a. Thereby, the reactions among the antigens A and the immobilized antibodies B1 at the sensor portion 65 are performed expediently and highly efficiently.

Step 6: Even in the case that the labeling antibodies BF which were not immobilized onto the sensor portion 65 remain on the sensor portion 65, the following plasma S functions as a cleansing agent that washes the labeling antibodies BF, which are floating or non specifically adsorbed onto the sensor portion 65, away. The plasma S which has passed over the sensor portion 65 is collected in a waste liquid reservoir 56.

As described above, the biological substance analyzing method of the second embodiment emits and controls ultrasonic waves such that a node of the standing wave U formed in the flow channel member 54 is positioned at the interface (matching interface 64a) between the acoustic matching layer 64 and the flow channel 52. Therefore, it becomes possible to concentrate the detection target substance in the vicinity of the sensor portion 65 by the capturing force that operates in the vicinity of the node. Thereby, expedient and highly efficient reactions are enabled between the detection target substance and the sensor portion 65. As a result, expedient and highly sensitive analysis and measurement becomes possible in biological substance analysis that detects detection target substances within the liquid sample S with the sensor portion 65 provided in the flow channel member 54.

The biological substance analyzing chip 50 and the biological substance analyzing apparatus of the second embodiment are equipped with the acoustic matching layer 64 that transmits ultrasonic waves at a predetermined region within the flow channel 52, such that the node of the standing wave U formed in the flow channel member 54 is positioned at the matching interface 64a. Therefore, it becomes possible to concentrate the detection target substance in the vicinity of the sensor portion 65 by the capturing force that operates in the vicinity of the node. Thereby, expedient and highly efficient reactions are enabled between the detection target substance and the sensor portion 65. As a result, expedient and highly sensitive analysis and measurement becomes possible in biological substance analysis that detects detection target substances within the liquid sample S with the sensor portion 65 provided in the flow channel member 54.

[Third Embodiment of the Biological Substance Analyzing Method and the Biological Substance Analyzing Apparatus]

Next, a biological substance analyzing method and a biological substance analyzing apparatus according to a third embodiment will be described. Note that the third embodiment will also be described as a case in which antigens and antibodies are employed as pairs of substances that specifically bind with each other, the detection target substance is an antigen, the binding substance that specifically binds with the detection target substance is an antibody, and analysis is performed by the sandwich method that employs fluorescent labels.

The biological substance analyzing method and the biological substance analyzing apparatus of the third embodiment differ from the second embodiment in that the sensor portion 65 within the chip is provided at a position on the surface of the inner wall of the flow channel 52 shifted in the longitudinal direction of the flow channel 52 from the surface of the acoustic matching layer 64 toward the side of the flow channel 52. Note that elements which are the same as those of the second embodiment will be denoted with the same reference numerals, and detailed descriptions thereof will be omitted insofar as they are not particularly necessary.

The biological substance analyzing method of the second embodiment employs an apparatus that includes a biological substance analyzing chip 50 equipped with a flow channel member 54 that forms a channel 52 for the liquid sample S that includes the antigens A to flow through, a flow inlet 54a, and an air opening 54b. An acoustic matching layer 64 and a sensor portion 65 are provided at a predetermined region of an inner wall of the flow channel member 54. The liquid sample S that includes antigens A, which have fluorescent labels, is supplied into the flow channel 52. Ultrasonic waves are emitted such that a standing wave U having a node positioned at the interface (matching interface 64a) between the acoustic matching layer 64 and the flow channel 52 is generated between the acoustic matching layer 64 and the inner wall of the flow channel member 54 that faces the acoustic matching layer 64. The antigens A are concentrated at the matching interface 64a by capturing forces that operate in the direction of the nodes. The concentrated antigens A are immobilized onto the sensor portion 65 by immobilized antibodies B1 which are immobilized on the sensor portion 65. Fluorescent signals from the fluorescent labels on the immobilized antigens A are detected, to analyze the presence or absence and/or the amount of the antigens A.

Figure 9:
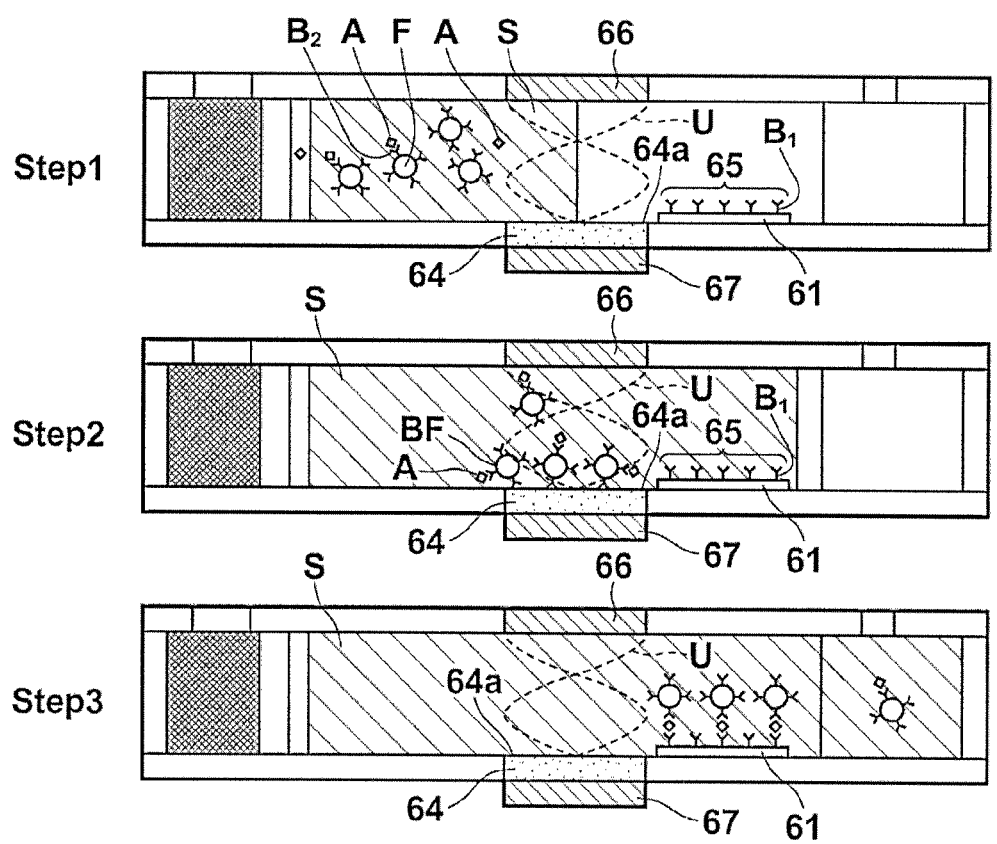
FIG. 9 is a diagram that illustrates the steps of a biological substance analyzing method that employs a biological substance analyzing chip according to a third embodiment of the present invention.

The biological substance analyzing chip 50 is equipped with the flow channel member 54 that forms the flow channel 52, through which the liquid sample that includes the antigens A is caused to flow, the flow inlet 54a connected to the flow channel, through which the liquid sample S is injected, and the air opening 54b through which the liquid sample S is expelled after flowing through the channel 52, as illustrated in FIG. 9. The acoustic matching layer 64 that transmits ultrasonic waves is provided at a predetermined region on the inner wall of the flow channel member 54 between the flow inlet 54a and the air opening 54b. The sensor portion 65 is provided on the surface of the inner wall of the flow channel 52 shifted in the longitudinal direction of the flow channel 52 from the surface of the acoustic matching layer 64 toward the side of the flow channel 52. The immobilized antibodies 31 that specifically bind with the antigens A are immobilized on the surface of the sensor portion 65.

In the third embodiment, the sensor portion 65 is provided at a position on the surface of the inner wall of the flow channel 52 shifted in the longitudinal direction of the flow channel 52 from the acoustic matching layer 64. That is, the sensor portion 65 may be provided at a position on the surface of the inner wall of the flow channel 52 shifted downstream from the acoustic matching layer 64, or provided to straddle a position directly on the acoustic matching layer 64 and the aforementioned shifted position. Note that the "longitudinal direction of the flow channel" refers to the direction along the flow channel 52, and the "position on the surface of the inner wall of the flow channel 52 shifted downstream from the acoustic matching layer 64" refers to a position on the surface of the inner wall that molecules within the liquid sample S will pass after passing through the vicinity of the acoustic matching layer, along with the flow of the liquid sample S.

The procedures by which an assay is performed according to the sandwich method to detect whether the antigen A, which is a detection target substance, is included in blood (whole blood) by the biological substance analyzing method of the third embodiment using the biological substance analyzing chip 50 will be described with reference to FIG. 9. The biological substance analyzing method of the third embodiment is performed by the same procedures as those of the analyzing method of the second embodiment up to and including Step 3 of FIG. 8. Accordingly, the procedures following the Step 3 of FIG. 8 will be described.

Step 1: the plasma S, which has leaked into the channel 52 and the labeling antibodies BF (the fluorescent particles F modified with the antibodies 32), which are provided within the channel 52, mix, and the antigens A within the plasma S bind with the labeling secondary antibodies BF. Meanwhile, ultrasonic waves are emitted to generate a standing wave U having a node positioned at the matching interface 64a.

Step 2: the antigens A are caused to be concentrated at the matching interface 64a, to enable expedient and highly efficient reactions among the antigens A and the immobilized antibodies 31 at the sensor portion 65.

Step 3: the plasma S gradually flows along the channel 52 toward the air opening 54b, and the antigens A, which are bonded to the labeling secondary antibodies BF, bind with the immobilized antibodies B1, which are immobilized onto the sensor portion 65. So called sandwich configurations, in which the antigens A are sandwiched between the immobilized antibodies 31 and the labeling antibodies BF, are formed. Even in the case that the labeling antibodies BF which were not immobilized onto the sensor portion 65 remain on the sensor portion 65, the following plasma S functions as a cleansing agent that washes the labeling antibodies BF, which are floating or non specifically adsorbed onto the sensor portion 65, away. The plasma S which has passed over the sensor portion 65 is collected in a waste liquid reservoir 56.

As described above, the biological substance analyzing method of the third embodiment emits and controls ultrasonic waves such that a node of the standing wave U formed in the flow channel member 54 is positioned at the interface (matching interface 64a) between the acoustic matching layer 64 and the flow channel 52. Therefore, it becomes possible to concentrate the detection target substance in the vicinity of the sensor portion 65 by the capturing force that operates in the vicinity of the node. Thereby, expedient and highly efficient reactions are enabled between the detection target substance and the sensor portion 65. As a result, expedient and highly sensitive analysis and measurement becomes possible in biological substance analysis that detects detection target substances within the liquid sample S with the sensor portion 65 provided in the flow channel member 54.

The biological substance analyzing chip 50 and the biological substance analyzing apparatus of the second embodiment are equipped with the acoustic matching layer 64 that transmits ultrasonic waves at a predetermined region within the flow channel 52, such that the node of the standing wave U formed in the flow channel member 54 is positioned at the matching interface 64a. Therefore, it becomes possible to concentrate the detection target substance in the vicinity of the sensor portion 65 by the capturing force that operates in the vicinity of the node. Thereby, expedient and highly efficient reactions are enabled between the detection target substance and the sensor portion 65. As a result, expedient and highly sensitive analysis and measurement becomes possible in biological substance analysis that detects detection target substances within the liquid sample S with the sensor portion 65 provided in the flow channel member 54.

(Design Modifications to the First through Third Embodiments)

The present invention is not limited to the first through third embodiments described above. For example, the embodiments were described as cases in which the sandwich method was employed. However, similar advantageous results can be obtained if the present invention is applied to immune measurements employing the competition method. In addition, antigens and antibodies were employed as the pair of substances that specifically bind with each other, and descriptions were given regarding antigen antibody reactions. However, the present invention exhibits similar advantageous effects in immune measurements that utilize protein cofactor reactions as well.

An embodiment that combines the second and third embodiments, that is, that in which the standing wave U is generated both upstream of the sensor portion and on the sensor portion to concentrate the detection target substance in two steps is preferable, because such an embodiment would enable even more expedient and highly efficient concentration of the detection target substance.

What is claimed is:

1. A biological substance analyzing method that employs a biological substance analyzing cell equipped with a reaction chamber having a sample supply space, an acoustic matching layer which is provided at a predetermined region of an inner wall of the reaction chamber that faces another inner wall, and a sensor portion provided on a surface of the acoustic matching layer toward the side of the sample supply space, on the surface of which an immobilized binding substance that specifically binds with the detection target substance is immobilized, comprising:
   supplying a liquid sample that includes a detection target substance into the sample supply space;
   emitting ultrasonic waves such that a standing wave having a node positioned at the interface between the acoustic matching layer and the sample supply space is generated between the acoustic matching layer and the other inner wall of the reaction chamber;
   concentrating the detection target substance at the interface by the capturing forces that operate in the direction of the nodes; and
   detecting the concentrated detection target substance with an immobilized binding substance, which is immobilized onto the sensor portion, that specifically binds with the detection target substance.

2. A biological substance analyzing cell, comprising:
   a reaction chamber that forms a sample supply space, into which liquid samples containing detection target substances are supplied;
   an acoustic matching layer provided at a predetermined region of an inner wall of the reaction chamber that faces another inner wall; and
   a sensor portion provided on a surface of the acoustic matching layer toward the side of the sample supply space, on the surface of which an immobilized binding substance that specifically binds with the detection target substance is immobilized.

3. A biological substance analyzing cell as defined in claim 2, further comprising:
   a reflecting layer provided at one of: the surface of the other inner wall of the reaction chamber that faces the acoustic matching layer so as to face the acoustic matching layer; and the surface of the acoustic matching layer opposite the side toward the sample supply space.

4. A biological substance analyzing cell as defined in claim 2, wherein:
   the sensor portion has at least one of a dielectric layer and a metal layer.

5. A biological substance analyzing chip, comprising:
   a flow channel member constituted by a flow channel through which liquid samples containing a detection target substance are caused to flow, a flow inlet connected to the flow channel for introducing the liquid samples into the flow channel, an air opening for causing the liquid samples which have been introduced into the flow channel to flow;
   an acoustic matching layer that transmits ultrasonic waves, provided at a predetermined region on the inner wall of the flow channel member between the flow inlet and the air opening; and
   a sensor portion provided at least one of the surface of the acoustic matching layer toward the side of the flow channel and at a position on the surface of the inner wall of the flow channel shifted in the longitudinal direction of the flow channel from said surface of the acoustic matching layer;
   an immobilized binding substance that specifically binds with the detection target substance being immobilized on the surface of the sensor portion.

6. A biological substance analyzing chip as defined in claim 5, further comprising:
   a reflecting layer provided at one of: the surface of the inner wall of the flow channel member that faces the acoustic matching layer so as to face the acoustic matching layer; and the surface of the acoustic matching layer opposite the side toward the flow channel.

7. A biological substance analyzing chip as defined in claim 5, wherein:
   the sensor portion has at least one of a dielectric layer and a metal layer.

8. A biological substance analyzing chip as defined in claim 5, further comprising:
   a label binding substance provided on the surface of the inner wall of the flow channel member upstream from the sensor portion;
   the label binding substance being:
   one of a first binding substance that specifically binds with the detection target substance and a second binding substance that competes with the detection target substance to specifically bind with the immobilized binding substance; and
   labeling particles modified with the one of the first binding substance and the second binding substance.

9. A biological substance analyzing apparatus, comprising:
   a biological substance analyzing cell as defined in claim 2;
   ultrasonic wave emitting means for emitting ultrasonic waves toward the interface between the acoustic matching layer and the sample supply space from a direction normal to the interface; and
   ultrasonic wave control means for controlling the ultrasonic wave emitting means such that a standing wave is generated on the interface and a node of the standing wave is positioned at the interface.

10. A biological substance analyzing apparatus, comprising:
- a biological substance analyzing chip as defined in claim 5;
- ultrasonic wave emitting means for emitting ultrasonic waves toward the interface between the acoustic matching layer and the flow channel from a direction normal to the interface; and
- ultrasonic wave control means for controlling the ultrasonic wave emitting means such that a standing wave is generated on the interface and a node of the standing wave is positioned at the interface.

* * * * *